United States Patent [19]

Neer et al.

[11] Patent Number: 4,698,328

[45] Date of Patent: Oct. 6, 1987

[54] METHOD OF INCREASING BONE MASS

[75] Inventors: Robert M. Neer, Cambridge; John T. Potts, Jr.; David M. Slovik, both of Newton, all of Mass.

[73] Assignee: The General Hospital Corporation, Boston, Mass.

[21] Appl. No.: 939,308

[22] Filed: Dec. 5, 1986

Related U.S. Application Data

[63] Continuation of Ser. No. 720,018, Apr. 4, 1985, abandoned.

[51] Int. Cl.$^4$ ............................................. A61K 37/36
[52] U.S. Cl. ....................................................... 514/12
[58] Field of Search ......................................... 514/12

[56] References Cited

U.S. PATENT DOCUMENTS 3,956,260  5/1976  Brugger et al. .
4,241,051  12/1980 Christie et al. .

OTHER PUBLICATIONS

Reeve, J. et al., British Medical Journal, 280: 1340 (1980).
Reeve, J. et al., in Monoclonal Antibodies and Developments in Immunoassay, p. 239, published Elsevier/North-Holland Biomedical Press, (1981).
Hefti, E. et al., Clinical Science, 62: 389 (1982).
Endo, H. et al., Nature, 286: 262 (1980).
Rader, J. I. et al., Calcified Tissue Research, 29(1): 21 (1979).
Wong, K. et al., Surgical Forum, 30: 100 (1979).
Peacock, M. et al., Vitamin D Proceedings Workshop, E. Norman, Editor, p. 411 (1977).
Mahgoub, A. et al., Biochemical and Biophysical Research Communications, 62: 901 (1975).
Dobroskok et al., "The Action of Parathyroid Hormone and Ca$^{45}$ on Rat Bone Tissue", translated from *Byulleten' Eksperimental'noi Biologii i Meditsiny*, vol. 77, No. 4, pp. 112–115, Apr. 1974.
Reiner et al., Revue du Rhumatisme, 1980, 47 (12), 699–706.
Tada et al., English abstract of Japanese Reference Biosis Number: 81048751, J JPN Soc Colo–Proctol 38 (6), 1985, 663–668, *Bone Metabolic Disorder During Steroid Therapy for Inflammatory Bowel Diseases*.
Podbesek et al., Clinical Science, 67:591–599 (1984).
Parsons et al., Biochemical Society Transactions, 9:383–386 (1981).
Podbesek et al., Medical Research Society, 57p, No. 165.
Crilly et al., Medical Research Society, 26p, No. 85.
J. Reeve, Clinical Endocrinology, 8:445–455 (1978).
Stevenson et al., Acta Endocrinologica, 104:462–467 (1983).
Kent et al., Clinical Science, 68:171–177 (1985).

*Primary Examiner*—Delbert R. Phillips
*Attorney, Agent, or Firm*—Saidman, Sterne, Kessler & Goldstein

[57] ABSTRACT

A method for increasing bone mass in a human afflicted with osteoporosis or a similar disease which comprises administering to the human so afflicted an effective amount of a composition comprising a parathyroid hormone or physiologically active fragment thereof, or equivalents thereof, in combination with either (a) a hydroxylated Vitamin D compound, or a structural or functional analogue thereof, or (b) a dietary calcium supplement. Pharmaceutical compositions containing the necessary components are also disclosed.

31 Claims, 1 Drawing Figure

METHOD OF INCREASING BONE MASS

This application is a continuation of application Ser. No. 720,018, filed Apr. 4, 1985, now abandoned.

BACKGROUND OF THE INVENTION

1. Field of the Invention

The present invention relates to a process for increasing bone mass in a human afflicted with osteoporosis.

2. Description of the Prior Art

Osteoporosis is a generic description for a group of diverse diseases which are characterized by a reduction in the mass of bone per unit volume with a histologically normal ratio of osteoid to bone. The effects of these diseases are particularly severe when the mass per unit volume decreases to a level below that required for adequate mechanical support. Osteoporosis is a particularly important cause of morbidity in the elderly. The most frequent symptoms are back pain and deformity of the spine resulting from a collapse of the vertebrae, especially in the lumbar and thoracic spine regions.

The problem presented worldwide by osteoporosis is truly staggering. It is estimated that in the United States alone, there are millions who symptomatically exhibit this disease. The disease appears to be an invariable accompaniment of aging, particularly among women, and the incidence is increasing with the age expectancy of the population. Osteoporosis often occurs when there is malnutrition, as a complication due to immobilization and paralysis, as a result of liver, kidney, or intestinal disease, and also after or during various forms of endocrine or rheumatic diseases. As improved public health measures increase life expectancy in third world nations and underdeveloped countries, the incidence of osteoporosis is beginning to be recognized as a significant problem in these countries as well. For these reasons, a treatment that can arrest the course of this widely present, destructive disease represents a significant medical advance.

Various methods have been discussed in the prior art for increasing bone mass in humans with osteoporosis. These treatments include administration of sodium fluoride, androgens, biologically active forms of parathyroid hormone alone, calcitonin, and calcitonin in combination with high dietary phosphate. Except for treatment with sodium fluoride, the effects of these treatments are modest. Sodium fluoride treatment increases trabecular bone in some patients but has uncertain effects on total bone mass and bone strength, a high risk of osteomalacia, as well as other unpleasant side effects.

In addition to these methods of treating osteoporosis by increasing bone mass, other methods are known which are designed to preserve existing bone mass. These methods involve the use of estrogens or calcium alone, or 1-hydroxy vitamin $D_3$ or 1,25-dihydroxy vitamin $D_3$ alone.

Typical publications disclosing and discussing these prior art methods include the following. Brugger et al., U.S. Pat. No. 3,956,260, discloses the preparation and use of a synthetic polypeptide for the treatment of osteoporosis. This polypeptide is unrelated to that of the present invention. Christie et al., U.S. Pat. No. 4,241,051, teaches topical application of the hormone calcitonin for the treatment of diseased bone in the ear.

Reeve et al., *British Medical Journal,* 280:1340 (1980), describes the results of a multicenter trial evaluating the effect of a fragment of human parathyroid hormone (hPTH (1-34)) on osteoporosis in humans. The authors report that this regimen resulted in a considerable increase in axial trabecular bone, but calcium retention, and hence, total bone mass, improved in only about half of these patients. In other patients calcium retention worsened and therefore, total bone mass decreased. The authors speculate that hPTH(1-34) might be most effective if administered in combination with estrogen, calcitonin, a diphosphonate, or some other agent that would limit resorption while allowing bone formation to continue.

Reeve et al., in *Monoclonal Antibodies And Developments In Immunoassay,* p. 239, published by Elsevier/North-Holland Biomedical Press (1981), report their progress towards answering some of the questions raised in the above study. The authors state that their studies of intestinal calcium absorption point to a possible defect in osteoporosis and further speculate that it may be necessary to circumvent this defect with, for example, 1,25-$(OH)_2$ vitamin $D_3$ in modest dosage, given during intervals when no hPTH injection is administered.

Hefti et al., *Clinical Science,* 62:389 (1982), describes studies using a high calcium diet supplemented with either parathyroid hormone or 1,25-$(OH)_2$ vitamin $D_3$ using normal and osteoporotic adult rats. The authors report that, although these studies showed an increase of whole-body calcium and skeletal mass, there was no restoration of individual trabeculae lost during the development of osteoporosis. Endo et al., *Nature,* 286:262 (1980), discuss the use of metabolites of vitamin D in conjunction with parathyroid hormone (PTH) to stimulate bone formation in vitro. However, these treatments with PTH and 1,25-$(OH)_2$ vitamin $D_3$ were no more effective than PTH alone in stimulating re-calcification of bone.

Rader et al., *Calcified Tissue International,* 29(1):21 (1979), describes the treatment of thyroparathyroidectomized rats with dietary calcium and intraperitoneal injectoion of a parathyroid extract. Although this treatment stimulated 1,25-$(OH)_2$ vitamin $D_3$ production and effected a marked increase in bone mineralization, it was also found to produce bone resorption as evidenced by the appearance of cavities in the cortical bone. There was no effect on rates of bone formation, or bone matrix apposition. Wong et al., *Surgical Forum,* 30:100 (1979), teach the administration to thyroparathyroidectomized dogs of daily intramuscular parathyroid extract or oral 1,25-$(OH)_2$ vitamin $D_3$ simultaneously with thyroid replacement therapy. The effect of these treatments on absorption of dietary calcium is discussed in the context of parathyroidism although not in the context of osteoporosis.

Peacock et al., *Vitamin D Proceedings Workshop.,* E. Norman, Ed., p. 411 (1977), disclose the inhibition by calcitonin and steroid sex hormones of the resorptive effect of vitamin D metabolites and parathyroid hormone on mouse calvaria bone in tissue culture. Pechet et al., *American Journal of Medicine,* 43(5):696 (1967), teach that minimum levels of parathyroid hormone are necessary in order for vitamin D to exert is effects on bone resorption rather than bone formation. In Mahgoub et al., *Biochemical and Biophysical Research Communications,* 62:901 (1975), the authors describe experiments and state that active vitamin D metabolites (25-OH vitamin $D_3$ and 1,25-$(OH)_2$ vitamin $D_3$) potentiate the ability of parathyroid hormone to elevate the cyclic AMP levels of cultured rat fetal bone cells.

None of these methods, however, have provided a clinically useful technique for treating osteoporosis and related disorders and often cause undesirable side effects. As a consequence, there is still a need for a generally effective treatment having minimal side effects.

SUMMARY OF THE INVENTION

Accordingly, it is an object of this invention to provide a method for increasing bone mass in a human afflicted with osteoporosis.

It is a further object of this invention to provide a pharmaceutical composition which can be used for increasing bone mass in a human afflicted with osteoporosis.

These and other objects of the invention, as will hereinafter become more readily apparent, have been accomplished by providing a method for increasing bone mass in a human which comprises administering to said human a parathyroid hormone or physiologically active fragment thereof, or equivalent thereof, in combination with (a) a hydroxylated vitamin D compound, or a structural or functional analogue thereof, or (b) a dietary calcium supplement.

DESCRIPTION OF THE PREFERRED EMBODIMENTS

Figure 1:
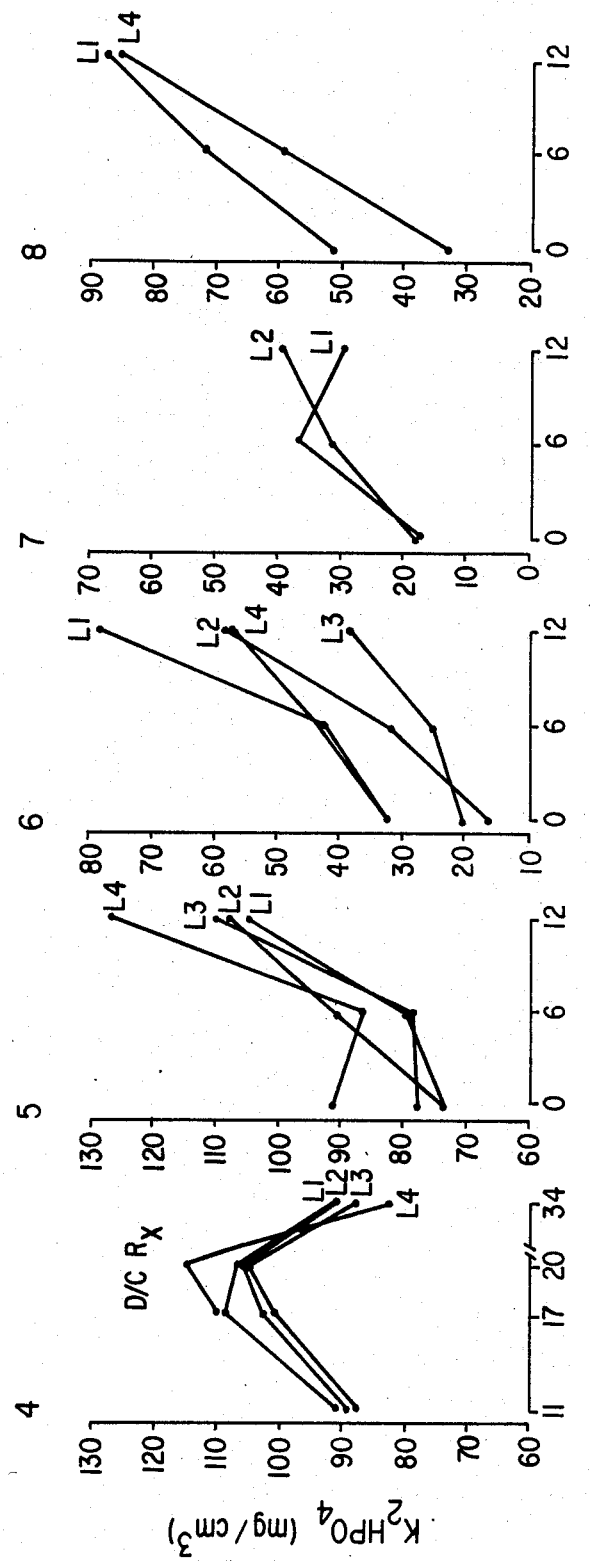
FIG. 1 shows the changes in trabecular bone density accompanying therapy according to the invention in five adult males with idiopathic osteoporosis.

The inventors have devised a method of increasing bone mass which represents a significant improvement over the prior art methods intended to accomplish this effect. The present invention comprises the administration, to a human afflicted with osteoporosis, of a combination of a parathyroid hormone or physiologically active fragment thereof, with either a hydroxylated vitamin D derivative, or a structural or functional analogue thereof, or a dietary calcium supplement. The invention also comprises pharmaceutical compositions intended for use in this method.

The parathyroid hormone appears to stimulate bone formation. The hydroxylated vitamin D component seems to act both to increase the intestinal absorption of calcium and to positively affect bone metabolism either directly or through its effects on calcium absorption from the intestines. Alternatively, a high calcium dietary supplement appears to increase calcium absorption from the intestines, thereby shifting the equilibrium of bone formation and bone resorption in favor of bone formation. The synergistic effects of these treatments are demonstrated hereinafter in clinical studies.

The present invention is intended to be used in all diseases classified as osteoporosis, particularly post-menopausal osteoporosis, senile osteoporosis, idiopathic osteoporosis, immobilization osteoporosis, post-partum osteoporosis, juvenile osteoporosis, and osteoporosis secondary to gonadal insufficiency, malnutrition, hyperprolactinemia, prolactinoma, disorders of the gastrointestinal tract, liver, or kidneys, and osteoporosis that is a sequella of prior osteomalacia, chronic acidosis, thyrotoxicosis, hyperparathyroidism, glucocorticoid excess or chronic disorders involving the bone marrow, and heritable forms of osteoporosis such as osteogenesis imperfecta and its variants, and other heritable disorders of connective tissue.

The first component involved in the method of the invention is a "parathyroid hormone," or fragment thereof hereafter abbreviated "PTHF." PTHF may consist of the first twenty-six, twenty-eight, thirty-four or any other physiologically active number of amino acids (numbered from the amino terminal) of a parathyroid hormone obtainable from a human or other vertebrate.

The term "obtainable" is intended to indicate that the PTHF is not necessarily derived from animal-produced parathyroid hormone but may be synthetically made, based on a natural model.

The term "fragment" is not intended to eliminate compounds larger or smaller than those specifically shown, but is intended to include all components obtainable from naturally occurring parathyroid hormones, up to and including or beyond the natural compounds themselves.

PTHF also encompasses chemically modified parathyroid hormone fragments which retain the activity associated with parathyroid hormone. The necessary activity is the stimulation of bone formation. Modifications that may be considered include:

(1) PTHF with carboxyl amino acid extensions beyond position 34 up to or beyond position 84 of the human PTH molecule, or amino-terminal extensions, or amino acid substitutions that produce other desirable features, such as an alpha-carboxyl amide at the carboxyl terminus. A desirable modification should delay metabolism and/or enhance activity in vivo;

(2) PTHF extended to include amino acids 1–38, which would enhance receptor binding and hence the activity per mole;

(3) PTHF with D-amino acid substitutions so as to delay metabolism and thereby enhance potency in vivo;

(4) PTHF chemically modified so as to enhance its absorption through the skin, mucous membranes, or gastro-intestinal tract to avoid thereby the necessity of parenteral injection; and (5) physiologically acceptable salts and esters of PTHF.

A PTHF obtainable from a mammal (PTHF 1–34) is generally preferred over other types of parathyroid hormone fragments, such as derivatives. Use of a PTHF consisting of the first thirty-four amino acid residues of human parathyroid hormone (hereafter abbreviated "hPTHF 1–34") is especially preferred for use in humans. Other preferred PTHF's are those which display some or all of the following desirable features: increased potency with regard to the necessary activity, increased ease of administration, increased selectivity to decrease potential side effects, and decreased antigenicity in humans to avoid an adverse immune response. PTHF molecules having the following formulas are particularly preferred:

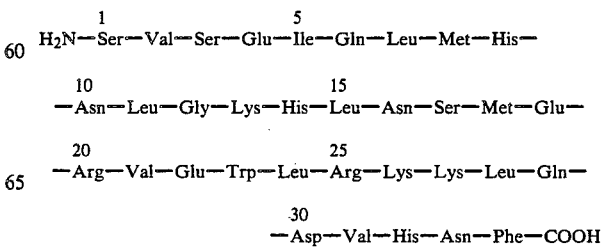

Ranges of administration of hPTHF 1-34, for example, are 100-700 units/day, more preferably 200-600 units/day, and most preferably 400-500 units/day, wherein "units" are defined in terms of the International Reference Preparation of hPTHF 1-34 and comparative bioassays in one of the established PTH bioassays. Potency ratios of different PTH analogues differ in different assays. The "units" are expressed in the chick hypercalcemic assay.

For other PTHF molecules, the ranges of administration are those high enough to stimulate bone remodeling in humans, yet not so high as to produce net bone resorption nor enough bone mineral mobilization to produce hypercalcemia or hypercalciuria. For compounds other than hPTH 1-34, dosage can be quantitated on a weight basis, or in terms of an appropriately established reference standard.

Hydroxylated vitamin D compounds of the invention include 1-alpha-hydroxy vitamin $D_3$ and 1-alpha,25-dihydroxy vitamin $D_3$ and their vitamin $D_2$ analogues: 1-alpha-hydroxy vitamin $D_2$ and 1-alpha,25-dihydroxy vitamin $D_2$. These molecules have the following formulas:

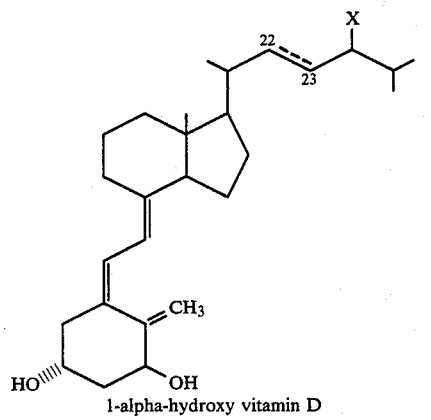
1-alpha-hydroxy vitamin D

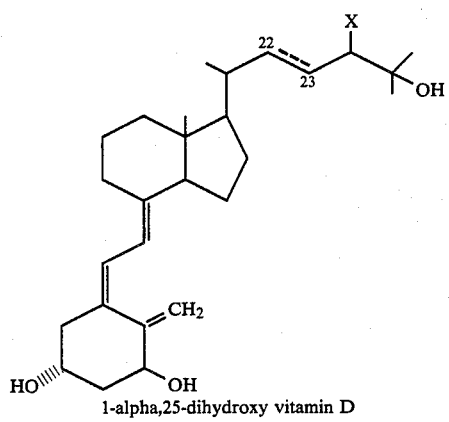
1-alpha,25-dihydroxy vitamin D wherein the bond between C-22 and C-23 may be single or double and wherein X may be H or —$CH_3$.

Chemical variations which retain the characteristics of these hydroxylated vitamin D molecules are contemplated as equivalents. Preferred are those like the glucuronide and sulfate derivatives of the above, dihydrotachysterol, 5,6-trans forms of vitamin D, and all other forms of vitamin D capable of stimulating the intestinal absorption of calcium without the necessity for prior hydroxylation at carbon 1 by the patient. Most preferred are compounds which also stimulate absorption of calcium for brief periods of time (days rather than weeks) after their administration is discontinued. These latter compounds are useful because they permit rapid reduction in biological effect in the event of overdose. Very large doses of vitamin D and 25-OH vitamin D stimulate the intestinal absorption of calcium without prior hydroxylation at carbon 1, but the resultant biological effects often last for weeks or months after administration of the drug has been halted, thus exposing the patient to a risk of toxicity.

The dose ranges for the administration of the vitamin D component are those large enough to produce the characteristic effects of vitamin D, particularly an enhanced intestinal absorption of calcium in osteoporotic patients, but not so large as to produce hypercalciuria or hypercalcemia. Possible dose ranges of various vitamin D analogues are illustrated in Table 1.

TABLE 1

| Vitamin D Analogue | RANGE[a] | | |
|---|---|---|---|
| | Broad | Preferred | Most Preferred |
| 1-alpha,25-$(OH)_2$ Vit $D_3$ or 1-alpha,25-$(OH)_2$ Vit $D_2$ | 0.05-2.0 | 0.1-1.0 | 0.25-0.50 |
| 1-alpha-OH Vit $D_3$ or 1-alpha-OH Vit $D_2$ | 0.05-3.0 | 0.1-1.5 | 0.25-0.75 |
| 25-OH Vit $D_3$ or 25-OH Vit $D_2$ | 10-150 | 20-100 | 20-50 |
| Vit $D_3$ or Vit $D_2$ | 1250 mcg. every 3 days to 3750 mcg/day. | 1250 mcg on alternate days to 2500 mcg/day. | 1250 mcg 3× weekly |
| dihydrotachysterol | 0.2-1.2 mg/day | 0.2-0.6 mg/day | 0.2-0.4 mg/day |

[a]Units in mcg/day unless otherwise noted.

By "dietary calcium supplement" as used in this invention is meant supplementing the normal diet with calcium at a level greater than that level which is recommended as the daily dietary allowance. In normal adult humans, the recommended daily allowance is 20-25 millimoles calcium/day and slightly higher in postmenopausal women, yet the customary intake of calcium among adults in the U.S. is only 12-18 millimoles/day. Since in many osteoporotic humans, the intestines are inefficient in absorbing calcium, this suboptimal calcium diet merely serves to aggravate their osteoporosis. Accordingly, a dietary calcium supplement for an adult would involve the administration of sufficient calcium to increase the total oral intake of diet plus supplement to 38-50 millimoles/day. When a dietary calcium supplement is used, the calcium is administered in a non-toxic form. The dosage rates mentioned herein refer to the amounts of calcium present, and the dosage rate of the actual compound used can be easily calculated therefrom using the formula weight of the compound being administered. Milk or any non-toxic salt of calcium may be utilized provided that the counter ion is not toxic to the human in which it is being administered. Typical suitable non-toxic counter ions include carbonate, citrate, phosphate, gluconate, lactate, chloride, and glycerol phosphate. The upper limit of the dietary calcium supplement is determined by the toxic effects of calcium, which varies slightly from patient to patient, as is well understood by those skilled in the art. Typically, in humans, the maximum allowance per day is 2000 mg calcium per day.

Use of the method of the invention is aided by pharmaceutical combinations comprising the ingredients intended for use in the method of the invention. Such pharmaceutical combinations were not suggested by the prior art since the method of the invention, which involves using specific combinations of ingredients, was unknown to the prior art.

By "pharmaceutical combination" as used herein is meant to include intimate mixtures of the two components of the invention, as in classical compositions, and also non-mixed associations, such as those found in kits or pharmaceutical packs.

A typical pharmaceutical mixed composition of the invention would contain PTHF in combination with a hydroxylated vitamin D compound or calcium in a form suitable for use as a dietary calcium supplement. The composition may additionally contain a pharmaceutically acceptable carrier and, if intended for oral administration, may comprise the PTHF in a liposome to protect this component.

The components can be administered parenterally by injection, rapid infusion, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance drug absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, such as wetting agents, emulsifying and suspending agents, and sweetening, flavoring, and perfuming agents.

The invention also relates to a method for preparing a medicament or pharmaceutical composition comprising the components of the invention, the medicament being used for increasing bone mass.

The materials for use in the administration of the invention are ideally suited for the preparation of a kit. Such a kit may comprise a carrier means being compartmentalized to receive in close confinement one or more container means such as vials, tubes and the like, each of said container means comprising one of the separate elements to be used in the method as well as such means as syringes and needles, sprays or dermal patches for administration of said elements.

For example, one of the container means may contain parathyroid hormone fragment (1-34) in lyophilized form or in solution. A second container may comprise a hydroxylated Vitamin D compound or a dietary calcium supplement in tablet form or in solution. The carrier means may also contain a third container means comprising a buffer solution for rehydrating lyophilized components present in the kit.

The above disclosure generally describes the present invention. A more complete understanding can be obtained by reference to the following specific examples which are provided herein for purposes of illustration only and are not intended to be limiting unless otherwise specified.

EXAMPLE 1

The effects of the methods and compositions of the invention were investigated in human patients. Three adult males afflicted with osteoporosis were given 500 units of a human parathyroid hormone fragment (hPTHF 1-34) and 0.25 ug of 1,25-dihydroxy vitamin $D_3$ (1,25-$(OH)_2D_3$) daily for a period of six to twelve months while consuming a normal calcium diet (15–20 mmoles/day). A fourth patient was given the same amount of parathyroid hormone fragment while receiving a high calcium intake (total intake more than 50 mmoles Ca/day). The effects of these treatments on calcium and phosphorus balances are shown in Table 2. The effect of these treatments on bone density is shown in Table 3.

The balance measurements involve complete collection and chemical analysis of all excreta for 18 days, during which the patient ate exactly the same foods each day. The minerals excreted were compared to those ingested to determine the total body retention, or "balance," for each patient. Cortical bone density was determined in the forearm by measuring the attenuation of radioactive $^{125}I$ photons by the shaft of the radius. Trabecular bone density was determined in the spine by quantitative computed x-ray tomography measurements of the lumbar vertebral bodies. These techniques are widely used for such purposes by those of skill in the art.

TABLE 2

| | Patient 1 hPTH + 1,25-$(OH)_2$ D | | | Patient 2 hPTH + 1,25-$(OH)_2$ D | | | Patient 3 hPTH + 1,25-$(OH)_2$ D | | | Patient 4 hPTH + Ca > 2 grams | | |
|---|---|---|---|---|---|---|---|---|---|---|---|---|
| | Pre | Rx | Delta | Pre | Rx | Delta | Pre | Rx | Delta | Pre | Rx | Delta |
| Calcium | | | | | | | | | | | | |
| Serum (mg %) | 9.19 | 9.44 | +0.25 | 9.24 | 8.75 | −.49 | 9.7 | 9.3 | −0.4 | 9.32 | 9.46 | +0.14 |
| Urine (mg/d) | 255 | 400 | +145 | 191 | 243 | +52 | 237 | 297 | +60 | 288 | 372 | +84 |
| Balance (mg/d) | −114 | −61 | +53 | −320 | +114 | +434 | −110 | −223 | −113 | −199 | +131 | +330 |
| Net Absorption | 136 | 339 | +203 | −129 | 345 | +474 | 103 | 123 | +23 | 90 | 499 | +409 |
| Phosphorus | | | | | | | | | | | | |
| Serum (mg %) | 4.34 | 3.99 | −.35 | 3.52 | 3.56 | +.04 | 4.5 | 4.0 | −0.5 | 3.55 | 3.59 | +0.04 |
| Urine (mg/d) | 1028 | 1073 | +45 | 805 | 548 | −257 | 459 | 768 | −309 | 1339 | 1400 | +61 |
| Balance (mg/d) | −254 | −142 | +112 | −262 | −213 | +475 | 173 | −90 | −263 | +33 | +188 | +155 |
| Net Absorption | 774 | 931 | +157 | 542 | 745 | +203 | 632 | 679 | +47 | 1372 | 1587 | +215 |

An improvement in calcium balance can be noted in Table 2. Failure to observe consistent improvement in calcium balance was one negative factor previously experienced with parathyroid hormone when it was administered without effort to augment intestinal absorption of calcium beyond provision of a diet containing the recommended dietary allowance for calcium.

Serial maintenance of cortical bone density in the forearm of three of these same patients are shown in Table 3. The control measurements were made over several months for each individual, and the values on treatment also reflect measurements made at intervals at several months each.

TABLE 3

| | Bone Densitometry ⅓ Distal (g/cm²) | | | |
|---|---|---|---|---|
| | Patient 1 | Patient 2 | Patient 3 | Patient 4 |
| Control | 0.75 | 0.74 | 0.80* | .625 |
| | 0.75 | 0.79 | 0.74 | .63 |
| | — | 0.78 | — | .613 |
| On Rx | hPTH + | hPTH + | hPTH + | hPTH + Ca |
| | (1,25-(OH)₂ D) | (1,25-(OH)₂ D) | (1,25-(OH)₂ D) | |
| | 0.67 | 0.79 | 0.71 | .61 |
| | 0.71 | 0.82 | 0.71 | .65 |
| | 0.69 | 0.83 | 0.69 | .60 |
| | 0.72 | — | 0.73 | .67 |
| | 0.74 | — | 0.70 | — |
| Off Rx | 0.75 (off Rx × 4 mos.) | 0.83 (off Rx × 1 yr.) | — | — |

*2½ years prior to initiation of treatment

Computerized tomography was used to measure bone density in the spine of patient 4. These measurements were performed on three lumbar vertebral (L1 through L3). A single 1 cm thick section was obtained through the mid-vertebral body using the scout view for localization. After the first series of scans, the patient was allowed to move freely before the duplicate set of measurements was taken. The results of the scans are shown in Table 4.

TABLE 4

| | Reading 1 | Reading 2 |
|---|---|---|
| Bone Density After 11 Months Of Treatment | | |
| L1 | 91.1 | 90.7 |
| L2 | 88.0 | 90.2 |
| L3 | 83.2 | 90.7 |
| Bone Density After 17 Months Of Treatment | | |
| L1 | 111 | 107 |
| L2 | 99 | 107 |
| L3 | 105 | 97 |
| Bone Density at End of Treatment | | |
| L1 | 104 | 109 |
| L2 | 110 | 104 |
| L3 | 106 | 107 |

The bone densities shown in Table 4 which were taken after eleven months of treatment are approximately 2 standard deviations below the mean for a man of this patient's age. By comparison, bone density measurements made at the end of treatment according to the method of the invention show an increase in bone density over the nine-month treatment interval of approximately 20%.

EXAMPLE 2

Five adult males with idiopathic osteoporosis were treated with hPTHF(1-34) and 1,25-(OH)₂ D₃ (patients 5-8) or with hPTHF(1-34) and calcium (patient 4) using dosages as described in Example 1. The results of this study are presented graphically in FIG. 1. The trabecular bone density measurements in individual lumbar vertebral bodies are expressed as K₂HPO₄ equivalents. All patients showed a significant increase in vertebral trabecular bone density during treatment.

Patient 4 showed a steady increase in bone densities until the twentieth month of therapy, at which time treatment was discontinued. When bone densities were measured fourteen months after the cessation of therapy, this patient's bone density had again declined. This further indicates the effectiveness of the combined therapy according to the invention in reversing the effects of osteoporosis on trabecular bone density of the vertebrae.

In patients 7 and 8, it was impossible to measure several of the vertebrae because of vertebral fractures preceding treatment. These figures denote a progressive and consistent improvement in the trabecular bone density of these patients.

Cortical bone density was measured in the forearm of these same patients prior to treatment and every three months during treatment. The density measurements showed no consistent change.

The invention now being fully described, it will be apparent to one of ordinary skill in the art that many changes and modifications can be made thereto without departing from the spirit or scope of the invention as set forth herein.

What is claimed as new and is desired to be covered by U.S. Letters Patent is:

1. A method of increasing bone mass in a human, which comprises:
   administering to said human a physiologically active parathyroid hormone or physiologically active fragment thereof, in combination with an agent selected from the group consisting of:
   (a) a hydroxylated Vitamin D compound, and
   (b) a dietary calcium supplement.

2. The method of claim 1, wherein said fragment consists of the first 34 amino acid residues of a parathyroid hormone obtainable from a human or animal.

3. The method of claim 1, wherein said fragment is obtainable from a human.

4. The method of claim 1, wherein said fragment has the amino acid sequence:

$$\begin{aligned} &\overset{1}{H_2N-Ser}-Val-Ser-Glu-\overset{5}{Ile}-Gln-Leu-Met-His- \\ &-Asn-Leu-Gly-Lys-\overset{15}{His}-Leu-Asn-Ser-Met-Glu- \\ &-\overset{20}{Arg}-Val-Glu-Trp-Leu-\overset{25}{Arg}-Lys-Lys-Leu-Gln- \\ &-\overset{30}{Asp}-Val-His-Asn-Phe-COOH \end{aligned}$$

5. The method of claim 1, wherein said administration of said hormone or said fragment is parenteral.

6. The method of claim 5, wherein said administration of said hormone or said fragment is by subcutaneous, intramuscular, or intravenous injection, nasopharyngeal or mucosal absorption, or trans dermal absorption.

7. The method of claim 1, wherein said administration of said hormone or said fragment is nonparenteral.

8. The method of claim 7, wherein said administration is by ingestion of liposomes.

9. The method of claim 1, wherein said parathyroid hormone fragment is administered at a rate of from 100 to 700 units per day.

10. The method of claim 1, wherein said agent is selected from the group comprising of: 1-hydroxy Vitamin D and 1,25-dihydroxy Vitamin D.

11. The method of claim 10, wherein said agent is 1,25-dihydroxy Vitamin D.

12. The method of claim 1, wherein said agent is a hydroxylated Vitamin D compound which is administered at a rate of from 0.05 to 150 mcg per day.

13. The method of claim 12, wherein said hydroxylated Vitamin D compound is administered at the rate of 0.05 to 3.0 mcg per day.

14. The method of claim 13, wherein said hydroxylated Vitamin D compound is administered at the rate of from 0.05 to 2.0 mcg per day.

15. The method of claim 1, wherein said agent is a dietary calcium supplement comprising a non-toxic calcium compound which is administered at a rate of greater than 2,000 mg/day in order to achieve a high calcium intake of 38–50 mmoles/day in adults.

16. A pharmaceutical combination comprising:
a physiologically active parathyroid hormone or physiologically active fragment thereof, in combination with an agent selected from the group consisting of:
(a) a hydroxylated Vitamin D compound, and
(b) a non-toxic calcium salt.

17. The combination of claim 16, wherein said parathyroid hormone fragment is a peptide consisting of the first 34 amino acid residues of a parathyroid hormone obtainable from a human or animal.

18. The combination of claim 16, wherein said hormone fragment is obtainable from a human.

19. The combination of claim 16, wherein said fragment has the amino acid sequence:

$$\begin{align}&\overset{1}{H_2N-Ser}-Val-Ser-Glu-Ile-\overset{5}{Gln}-Leu-Met-His-\\&\overset{10}{-Asn}-Leu-Gly-Lys-His-\overset{15}{Leu}-Asn-Ser-Met-Glu-\\&\overset{20}{-Arg}-Val-Glu-Trp-Leu-\overset{25}{Arg}-Lys-Lys-Leu-Gln-\\&\overset{30}{-Asp}-Val-His-Asn-Phe-COOH\end{align}$$

20. The pharmaceutical combination of claim 16, wherein said combination comprises from 100 to 700 units of said parathyroid hormone fragment.

21. The pharmaceutical combination of claim 20, wherein said combination comprises from 200 to 600 units of said parathyroid hormone fragment.

22. The pharmaceutical combination of any of claims 19 and 21, wherein said combination comprises from 400 to 500 units of said parathyroid hormone fragment.

23. The combination of claim 16, wherein said agent is selected from the group consisting of: 1-hydroxy Vitamin D or 1,25-dihydroxy Vitamin D.

24. The combination of claim 23, wherein said agent is 1,25-dihydroxy Vitamin D.

25. The combination of claim 16, wherein said agent is from 0.05 to 150 mcg of said Vitamin D compound.

26. The combination of claim 25, wherein said agent is from 0.05 to 3.0 mcg of said Vitamin D compound.

27. The combination of claim 26, wherein said agent is from 0.05 to 2.0 mcg of said Vitamin D compound.

28. The combination of claim 16, wherein said agent is comprises calcium coupled to a non-toxic counter ion.

29. The combination of claim 28, wherein said non-toxic counter ion is carbonate, citrate, phosphate, gluconate, lactate, chloride and glycerol phosphate.

30. The combination of claim 29, wherein said calcium salt is calcium carbonate.

31. The combination of claim 16, wherein said agent is from 12.5 to 50 mmoles of said calcium salt.

* * * * *

UNITED STATES PATENT AND TRADEMARK OFFICE
CERTIFICATE OF CORRECTION

PATENT NO. : 4,698,328
DATED : October 6, 1987
INVENTOR(S) : Neer et al.

It is certified that error appears in the above—identified patent and that said Letters Patent is hereby corrected as shown below:

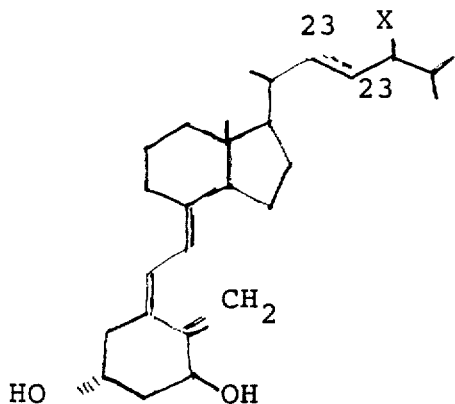

The correct structure for 1-alpha-hydroxy vitamin D is shown at left. An incorrect structure is shown in column 5, lines 25-39.

Claim 15, line 4 should read-- no greater than 2,000 mg/day in order to achieve a high--

Signed and Sealed this

Twentieth Day of December, 1988

Attest:

DONALD J. QUIGG

Attesting Officer

Commissioner of Patents and Trademarks